(12) United States Patent
Turner et al.

(10) Patent No.: US 8,177,725 B2
(45) Date of Patent: *May 15, 2012

(54) REFLEXOMETRY AND HORMONE FUNCTION

(76) Inventors: Daryl V. Turner, Scottsdale, AZ (US); Konrad Kail, Phoenix, AZ (US)

(*) Notice: Subject to any disclaimer, the term of this patent is extended or adjusted under 35 U.S.C. 154(b) by 62 days.

This patent is subject to a terminal disclaimer.

(21) Appl. No.: 12/764,683

(22) Filed: Apr. 21, 2010

(65) Prior Publication Data

US 2010/0204607 A1 Aug. 12, 2010

Related U.S. Application Data

(62) Division of application No. 11/560,798, filed on Nov. 16, 2006, now Pat. No. 7,708,699.

(60) Provisional application No. 60/738,396, filed on Nov. 18, 2005.

(51) Int. Cl.
*A61B 19/00* (2006.01)

(52) U.S. Cl. .................. 600/553; 600/587; 436/500

(58) Field of Classification Search .......... 600/553, 600/587, 531; 436/500
See application file for complete search history.

(56) References Cited

U.S. PATENT DOCUMENTS

| | | | | |
|---|---|---|---|---|
| 3,200,814 A * | 8/1965 | Rhein et al. | .......... | 600/553 |
| 3,322,115 A * | 5/1967 | Richards | .......... | 600/553 |
| 3,626,927 A * | 12/1971 | Breneman | .......... | 600/553 |
| 3,734,082 A * | 5/1973 | Rawson et al. | .......... | 600/553 |
| 3,739,768 A * | 6/1973 | Rieth | .......... | 600/553 |
| 3,799,740 A * | 3/1974 | Mincey | .......... | 436/500 |
| 3,938,503 A * | 2/1976 | Vis | .......... | 600/553 |
| 4,478,945 A * | 10/1984 | Lee et al. | .......... | 436/500 |
| 5,551,446 A * | 9/1996 | Chutkow et al. | .......... | 600/595 |
| 5,582,183 A | 12/1996 | Breneman | | |
| 5,913,831 A | 6/1999 | Breneman | | |
| 6,306,102 B1 * | 10/2001 | DeBolt | .......... | 600/558 |
| 6,716,427 B1 * | 4/2004 | Donovan | .......... | 424/94.5 |

(Continued)

FOREIGN PATENT DOCUMENTS

GB 1383958 2/1975

OTHER PUBLICATIONS

Daag International, Inc., PCT International Search Report dated Jun. 8, 2007, International Application No. PCT/US2006/044784, (Jun. 8, 2007).

(Continued)

*Primary Examiner* — Max Hindenburg
*Assistant Examiner* — Michael C. Stout
(74) *Attorney, Agent, or Firm* — Blakely Sokoloff Taylor & Zafman LLP

(57) ABSTRACT

A method including measuring time periods in which a reflex point of a subject is struck and a reflex response is observed. A method including determining a resting metabolic rate of a subject by applying the Kail-Waters equation. An apparatus including a striking instrument capable of delivering a kinetic energy to a reflex point of a subject; and a measurement instrument capable of being coupled to a subject and measuring a reflex response. A machine-readable storage medium containing executable program instructions which when executed cause a digital processing system to perform a method including determining time periods in which a reflex point is struck and a reflex response is observed. A machine-readable storage medium containing executable program instructions which when executed cause a digital processing system to perform a method including determining a resting metabolic rate of a subject by applying the Kail-Waters equation.

13 Claims, 6 Drawing Sheets

U.S. PATENT DOCUMENTS

| | | |
|---|---|---|
| 7,034,694 B2 * | 4/2006 | Yamaguchi et al. ........ 340/573.1 |
| 2002/0120209 A1 * | 8/2002 | Colloca et al. ................. 600/546 |
| 2002/0123521 A1 * | 9/2002 | Lavin ............................. 514/381 |
| 2002/0133093 A1 * | 9/2002 | Mayrose et al. ............... 600/587 |
| 2002/0156399 A1 * | 10/2002 | Kanderian et al. ............ 600/587 |
| 2003/0054571 A1 * | 3/2003 | Watkins et al. ............... 436/526 |
| 2004/0077556 A1 * | 4/2004 | Chinery ........................... 514/27 |
| 2004/0157809 A1 * | 8/2004 | De Zegher et al. ............ 514/171 |
| 2005/0059902 A1 * | 3/2005 | Itagaki ........................... 600/547 |
| 2005/0113703 A1 * | 5/2005 | Farringdon et al. ............ 600/509 |
| 2005/0172311 A1 * | 8/2005 | Hjelt et al. ....................... 725/10 |
| 2005/0228237 A1 * | 10/2005 | Shallenberger ............... 600/300 |
| 2007/0118046 A1 * | 5/2007 | Turner et al. .................. 600/553 |
| 2007/0178604 A1 * | 8/2007 | Watkins et al. ............... 436/500 |
| 2010/0178381 A1 * | 7/2010 | MacGibbon et al. ............. 426/2 |

OTHER PUBLICATIONS

Knappe, Von G., et al., "Achilles Tendon Reflexometry in the Diagnosis of Thyroid Gland Diseases Die Achillessehnenreflexometrie in der Diagnostik der Schilddrusenerkrankungen", Zeitschrift Fur Arztliche Fortbildung, Jena, DD, vol. 65, No. 6, Mar. 15, 1971, XP009083666, ISSN: 0044-2178, (Mar. 15, 1971), 289-293.

* cited by examiner

REFLEXOMETRY AND HORMONE FUNCTION

CROSS-REFERENCE TO RELATED APPLICATION

This application is a divisional of co-pending U.S. patent application Ser. No. 11/560,798, filed Nov. 16, 2006, which claims the benefit of the earlier filing date of U.S. Provisional Patent Application No. 60/738,396, filed Nov. 18, 2005.

FIELD

Reflexometry and hormone function.

BACKGROUND

Thyroid dysfunction affects more than 30 percent of the U.S. population. Sub-clinical hypothyroidism appears to greatly affect the subject's health risk of many chronic degenerative diseases. The risks associated with sub-clinical hypothyroidism can be grouped into the following risk categories: Cardiovascular Risk, Diabetes Risk, Arthritis and Inflammatory Risk, Neurological Risk, Bone Risk and Pregnancy complications.

The current methods of testing for thyroid hormone dysfunction include the "gold standard," which is resting metabolic rate, and serum thyroid measurements.

Reflexometry was studied in the 1960's and 1970's with Achilles tendon reflexometry, and various pieces of testing equipment were developed, which gave somewhat varied results. They were difficult to operate and use on a subject, and were never widely accepted. The original studies looked at the height of the waveform and the length of the firing interval.

It was determined that the height of the waveform did not correlate with thyroid events. It was found, however, that the descending slope of the firing interval was elongated with the point of least variance at half of relaxation. This was difficult to determine.

DETAILED DESCRIPTION

Figure 1A:
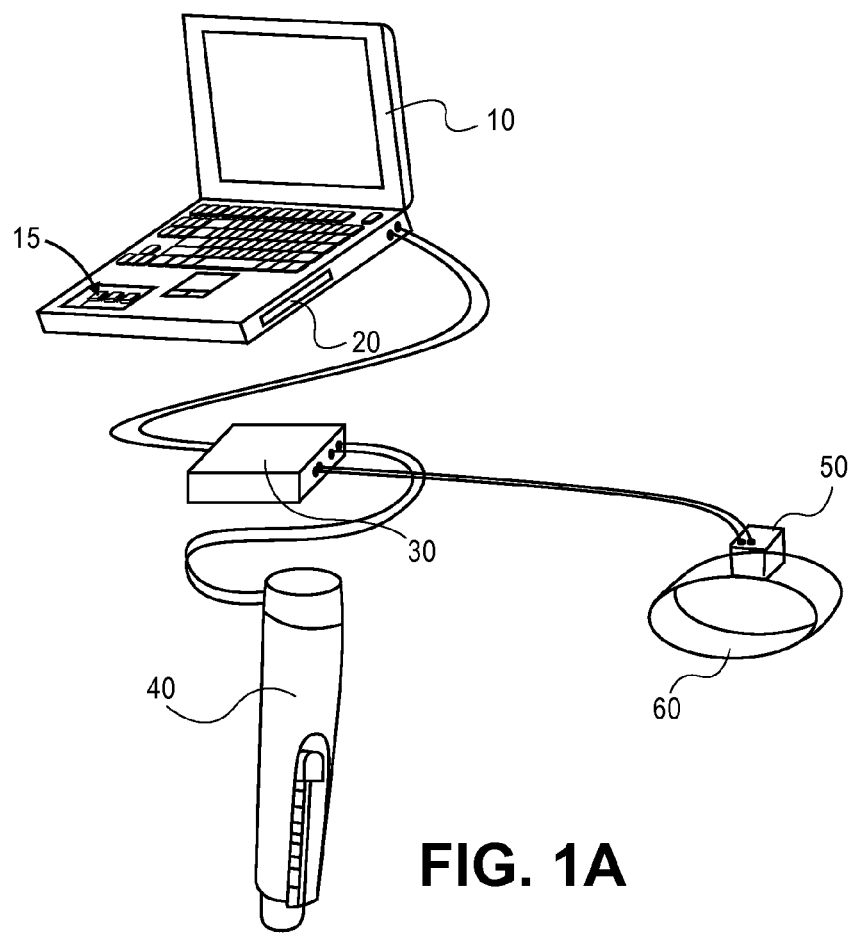
FIG. 1A shows a schematic view of an embodiment of a Brachioradialis reflexometry system.

In one embodiment, a device, a system and a method are described that correlate a reflex response to a hormone function. As an example, a device, a system and a method are described that correlates a resting metabolic rate that may be used to assess thyroid function with Brachioradialis Reflex intervals. The device, system and method may also be used with other reflex points located on the body of a human or animal with the establishment of appropriate parameters for those reflex points and to assess other hormone functions. By way of example, the effect of a substance (e.g., magnesium) on pre-eclamptic women may be evaluated using the device, system and method described herein.

In one embodiment, a device and system includes three components—a machine-readable medium (e.g., software), a striking instrument such as a spring-loaded plunger/hammer capable of delivering kinetic energy to a reflex point, and a measuring instrument such as an inclinator capable of measuring a reflex response.

In one embodiment, the machine-readable medium includes a program (e.g., a software program) that incorporates the capture of time intervals picked up by sensors in a striking instrument and a measuring instrument, and to integrate the time intervals into a statistical analysis model, that produces results, which may be displayed to an operator, in the form of a numbers or a graph. For example, the time intervals data may be integrated with a subject's data, by way of example, height, weight, and other factors, and a resultant output of resting metabolic rate is calculated. The resting metabolic rate and/or speed of the reflex may then be used by a medical professional, caregiver, or the subject himself/herself to assess thyroid function or the effect of any medication on thyroid function. Alternatively, the program (e.g., software program) may include instructions that assess thyroid function or the effect of any medication on thyroid function based on resting metabolic rate and/or speed of the reflex.

In terms of capturing time intervals, in one embodiment, a sensor in the striking instrument and a sensor in the measuring instrument permit the measurement of a Pre-Firing Interval and a Firing Interval with regard to a reflex response. Using the Brachioradialis as an example, a "Pre-Firing Interval" is defined as the number of milliseconds from a strike at the trigger point of the Brachioradialis by a striking instrument to initiation of the Brachioradialis reflex response. A "Firing Interval" is defined as the number of milliseconds from initiation of the Brachioradialis reflex firing until its return to baseline. "Firing Interval minus Pre-Firing Interval" is the difference in milliseconds between those intervals.

In one embodiment, the striking instrument includes a spring-loaded plunger or other design for striking a reflex point (e.g., including but not limited to a manual drop weight). Using the Brachioradialis as an example, the striking instrument (e.g., spring-loaded plunger or other device), when released, can accelerate towards the Brachioradialis and strike a Brachioradialis reflex point in such a way as to cause an involuntary reaction in the form of a reflex arc of the Brachioradialis.

In one embodiment, the firing of the spring-loaded plunger may be performed one to five times or more, with software recording each measurement and the number of tests, and the software averages or means the results of the time intervals for both the Pre-Firing Interval and the Firing Interval, and the Pre-Firing Interval minus the Firing Interval.

In one embodiment, the measuring instrument is capable of detecting the reflex arc caused by the striking of a reflex point by the striking instrument. Suitable measuring instruments include, but are not limited to, an inclinator that measures tilt (e.g., a distance from level) or other device that is capable of sensing movement of a finger or hand (e.g., laser, opposing electrical contacts, etc.). Using a measuring instrument that is an inclinator as an example, for measuring a reflex response of the Brachioradialis reflex, the inclinator is placed on a subject's wrist or finger by the way of a strap and this tilt device records the movement of the wrist caused by the reflex reaction.

A representative method of striking and measuring a Brachioradialis reflex to, for example, determine metabolic rate and a correlation to thyroid function includes placing a subject's arm on a flat surface so that the surface fully supports the weight of the arm and a hand is left to hang fully relaxed over the end of the flat surface in a dependent manner, so that it can be freely moved up and down without any obstructions, or impedance to movement. A measuring device such as an inclinator is attached to the subject's wrist, or hand or finger with the inclinator being positioned on top of the subject's wrist, and in line with the middle finger.

The Brachioradialis reflex firing point is located by extending the subject's hand fully back, and requiring the subject to move his/her middle finger. With this exercise, the Brachioradialis can be seen or felt. This may also be accomplished by tapping with a finger on the subject's forearm, until a reflex reaction is seen in the subject's said finger. Having identified a reflex point, the reflex point may be marked at the reflex location on the forearm.

A striking instrument such as a spring-loaded plunger is 'cocked' or engaged and then placed against the Brachioradialis trigger point. The spring-loaded plunger is then released, striking the surface skin of the subject's forearm at the marked reflex point, and transferring its kinetic energy into the Brachioradialis. The striking of the skin, in one embodiment, begins the Pre-Firing Interval that is captured by a computer program to which the plunger is connected and recorded by the program.

The Brachioradialis reacts to the strike by the spring-loaded plunger with an involuntary reaction in the form of a reflex response, by sending a signal via the nerves and neurotransmitter chemicals to the spinal cord then back down to the targeted muscle, instructing the Brachioradialis muscle to react in the form of an involuntary reflex.

The involuntary reflex of the Brachioradialis muscle causes the hand and a finger of the subject to inclinate in an up and down motion, the beginning of which ends the Pre-Firing Interval and the beginning and end of which is the Firing Interval. The inclination of the hand/finger is detected by the measuring instrument that, in one example, is an inclinator attached to the subject's hand, and is captured by a computer program to which the inclinator is connected and recorded by the program.

In one embodiment, a computer program (software instruction logic) takes the information from the firing of the spring-loaded plunger and the motion, captured by the inclinator, and intervals (Pre-Firing Interval and Firing Interval) are displayed on, for example, a computer useable interface linked to the software instruction logic, in the form of numerical data points or a graph. In the case of a graphical display, an operator places markers where the reflex motion intersects with the base line. The system then calculates the times for the Firing Interval, the Pre-Firing Interval and Firing Interval minus Pre-Firing Interval. The resultant information is then displayed as discussed in the following text.

The Firing Interval, Pre-Firing Interval and Firing Interval minus Pre-Firing Interval information is used to correlate via, for example, a statistical analysis model, a resting metabolic rate. Resting metabolic rate is generally how many calories an individual burns per day at rest, which is generally related to, among other things, an individual's height and weight. Resting metabolic rate is effected by factors such as sex, age, weight, and height of a subject. With regard to sex, an average male subject typically has a higher resting metabolic rate than an average female subject. Similarly, a younger average subject typically has a higher resting metabolic rate than an average older subject of the same sex.

In one embodiment, the calculated resting metabolic rate as correlated to the reflex tests carried out on the subject and a measured metabolic rate, which is the current gold standard for determining thyroid function, are linked in a later principal components analysis model.

FIG. 1A shows an embodiment of a Brachioradialis reflexometry system. In this embodiment, the system includes: computer 10 including memory 15 to which is stored data from measuring devices including data related to Pre-Firing Interval and Firing Interval; software instruction logic (hereinafter "software") 20 (e.g., a computer program embedded in a machine-readable medium) added to computer 10 to analyze the incoming data from the measuring devices including to calculate the Firing Interval minus Pre-Firing Interval, and the resting metabolic rate; electronic recording device 30 which controls the input from the measuring devices and sends the data to the software (e.g., receives electrical impulses or signals and transmits such signals in digital form to software 20); spring loaded plunger 40 that may be cocked and fired at the Brachioradialis firing point, delivering a consistent transfer of potential energy to the surface of the skin, which is transformed into kinetic energy as it enters the Brachioradialis and triggers the involuntary reflex response that plunger 40 then sends to software 20; inclinator 50 that picks up the tilt of a dependent and unhindered hand/finger, sending the tilt information to software 20 (e.g., movement of the unhindered hand/finger in response to a reflex response); and wristband 60 that is connected to inclinator 50 and that secures inclinator 50 in place to a dependent and unhindered hand/finger of a test subject, allowing the hand to move in a reflex response. An example of a suitable plunger is a plunger sold by Paladin Tools modified to transmit electrical signals. As example of a suitable inclinator is a tilt sensor available from U.S. Digital Corporation.

Software 20 is a computer program stored in a machine-readable storage medium (e.g., a computer-readable storage medium) such as memory 15 and computer 10. Memory 15 may be a hard disk drive, but may also be other kinds of memory. A representative computer program includes, among other things, subsequent instructions that dictate the receipt of data related to a Pre-Firing Interval, Firing Interval, instruction to calculate Firing Interval minus a Pre-Firing Interval, as well as an instruction that may relate to the collection of a subject's height, weight and body mass index, that may be used to calculate a resting metabolic rate. It is to be appreciated that other computer programs such as one stored on another memory device, included, but not limited to, a disk, may also be used. The computer program is processed by a processor in computer 10. The interface between a user and computer 10 may be implemented, for example, via a monitor with command instruction implemented by an interface such as a keyboard, mouse, light-pen sensor or touch screen monitor.

Figure 1B:
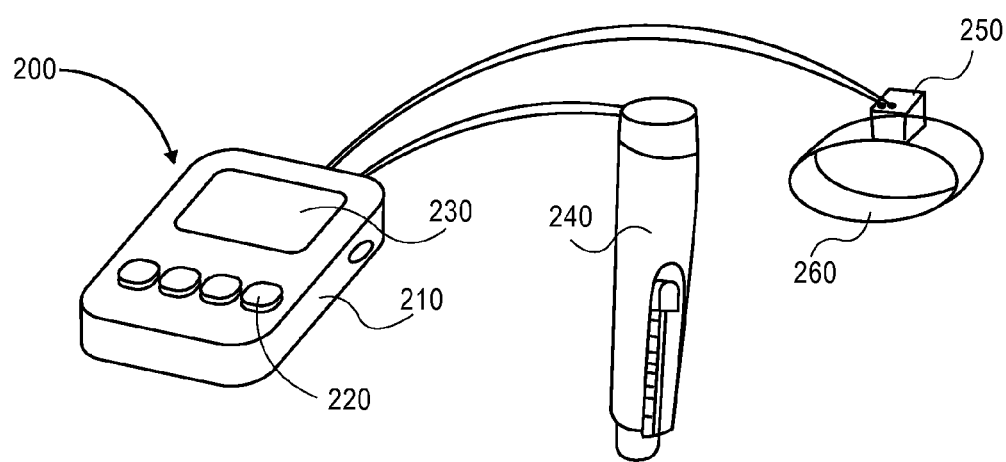
FIG. 1B shows a schematic view of another embodiment of a Brachioradialis reflexometry system.

FIG. 1B shows an embodiment of a portable version of the Brachioradialis Reflexometry system that may be used by a medical professional or a person in the privacy of their own space to test for thyroid function, allowing the professional or person upon viewing the results to adjust medication if necessary or seek professional help. The system includes computer 200, including software (e.g., a computer program) and electronic recording device incorporated into a handheld device 210, with input buttons 220 and display screen 230. In one embodiment, computer 200 also includes a memory capable of storing data, including data related to Firing Interval, Pre-Firing Interval, resting metabolic rate, height, weight, and age. The system also includes spring loaded plunger 240 that may be cocked and fired at the Brachioradialis firing point delivering a consistent transfer of potential energy to the surface of the skin, which is transformed into kinetic energy as it enters the Brachioradialis and triggers the involuntary reflex response. Plunger 240 then sends information to the software (e.g., time of firing). The system further includes inclinator 250 that picks up the tilt of a dependent and unhindered hand/finger sending the information to the software regarding a first time for an initiation of a reflex response a second time for a completion of the reflex response. Still further, the system includes wristband or finger band 260 connected to inclinator 250 to secure the inclinator in place to the dependent and unhindered hand/finger, allowing the hand or finger to move freely in a reflex response.

Figure 2:
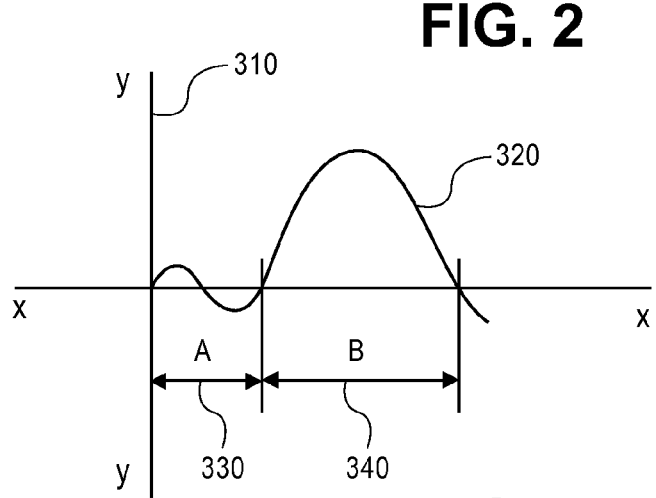
FIG. 2 shows a xy graphical representation of a Pre-Firing Interval and a Firing Interval associated with a reflex response.

FIG. 2 shows the 'X' and 'Y' coordinates on graph 310 to record the time intervals of Pre-Firing Interval and Firing Interval with a baseline; resultant graph trace 320, after the event, showing where the graph crossed the baseline, creating Pre-Firing Interval 330 and Firing Interval 340. Pre-Firing Interval 330 and Firing Interval 340 correlate the data to the Harris Benedict resting metabolic rate equation. Pre-Firing Interval 330 shows the time interval as the ascending bell curve trace crosses the baseline. Firing Interval 340 shows the time interval as the descending bell curve trace crosses the baseline. The two intervals are then computed into a Reflex Time Interval of Firing Interval 340 minus Pre-Firing Interval 330, resting metabolic rate and the Kail-Waters equation.

Figure 3:
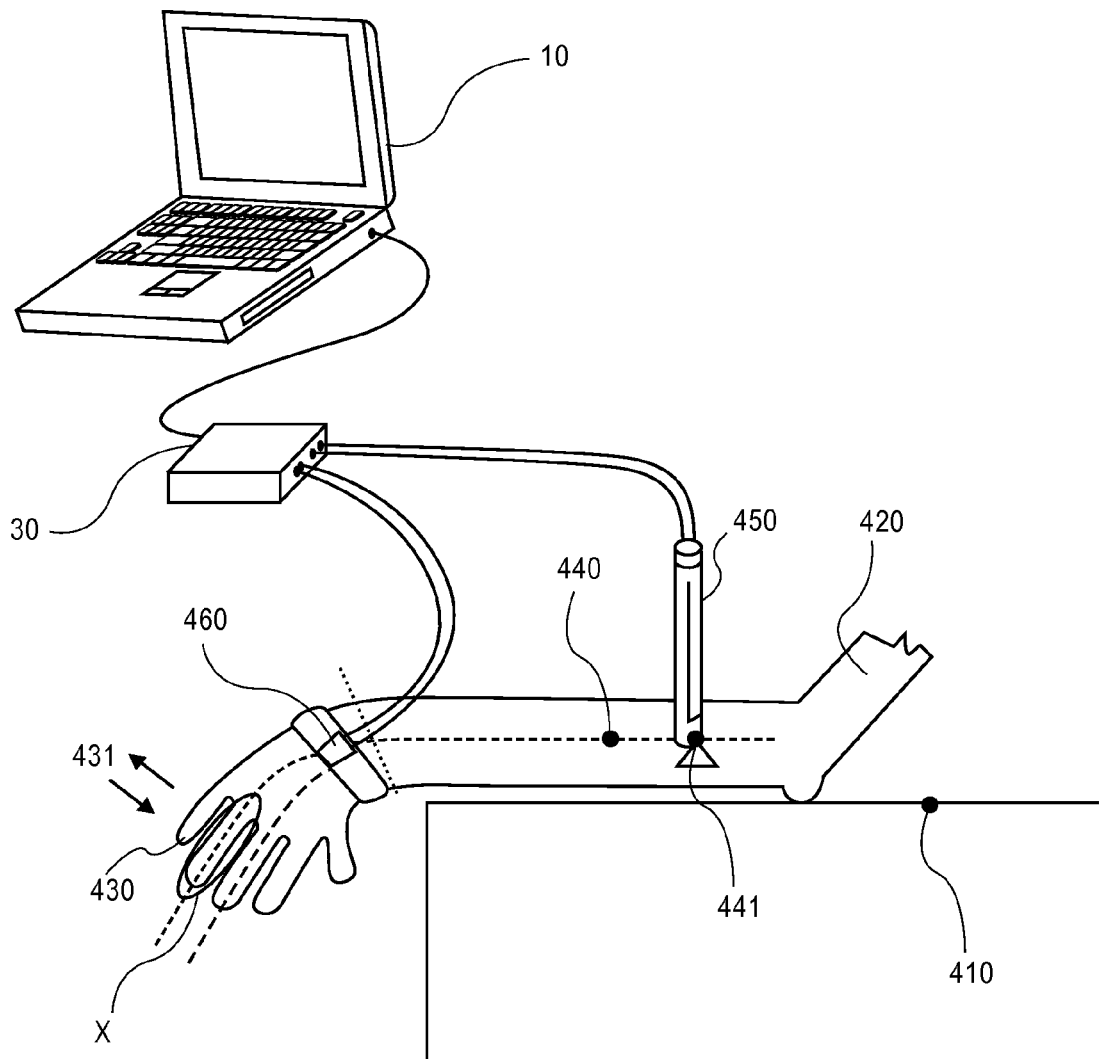
FIG. 3 shows a schematic view of a forearm of a human subject resting on a surface and demonstrates the monitoring of a reflex response.

FIG. 3 shows flat surface 410, preferably a table top, to support a subject's arm. In one embodiment, a subject is seated next to surface 410 with the subject's arm 420 resting on surface 410, with hand 430 positioned dependent and unhindered off an end of surface 410. A firing point (i.e., Brachioradialis firing point 441) for reflex movement 431 of Brachioradialis tendon 440 is located by tapping the appropriate location on the forearm, and receiving a reflex response, or by the subject flexing the hand back and moving the middle finger. Inclinator 460 is placed, in one embodiment, on the subject's wrist or finger through a wrist/finger band and spring loaded plunger 450 is positioned over Brachioradialis firing point 441. Spring loaded plunger 450 is then fired one or more times to trigger an involuntary reflex response by the Brachioradialis. Inclinator 460, attached to a wrist/finger band, allows the hand/finger to move in a reflex response and the response is captured and sent to a computer program (software). A Pre-Firing Interval is captured by a computer memory directed by the software as a first time that spring-loaded plunger 450 contacts Brachioradialis firing point 441 of the subject and sends a message for the reflex to fire and a second time at the initiation of a reflex response. The Firing Interval is captured by the computer memory directed by software of a first time corresponding to an initiation of a reflex response and a second time corresponding to a conclusion of a reflex response. The software may then calculate a Firing Interval minus Pre-Firing Interval and with information on the subject's height and weight, determine a resting metabolic rate.

As described above, an object of the device, the system and the method is a non-invasive reflex test that is easy to use by a physician or their trained staff and a reflex method that could be used by the subject themselves, on themselves, in their own homes, to enable them to monitor the function of their thyroid and/or the effect of the medications that they are/were taking, enabling them to refer the result of any test to a physician or to alter their dose accordingly, similar to the at-home testing for diabetics. Determining time periods in which a reflex point is struck until an initiation of a reflex response is observed as heretofore generally been done by a physician through the physician's trained visual observation of the reflex response. It is appreciated that visually observing millisecond differences, e.g., 100 milliseconds vs. 150 milliseconds is very challenging. The device, system and method remove this challenge by measuring the time periods with devices (e.g., plunger, inclinator) that can identify or be calibrated to detect millisecond time periods.

The medical literature has identified several risks associated with thyroid dysfunction. These risks include:

Cardiovascular Risk—Several investigators have shown an increase in dyslipidemia, homocysteine, C-reactive protein, coronary artery disease, hypertension, and ischemic heart disease in people with sub-clinical hypothyroid.

Several investigators have also found hypercoaguability, endothelial dysfunction, and peripheral arterial disease. Ripoli measured decreased cardiac preload and increased afterload resulting in decreased stroke volume and cardiac output.

Diabetes Risk—McCluskey showed that disruption of GLP-1 signaling affected corticosteroid and thyroid responses to stress in mice. Schultes demonstrated that in humans, hypoglycemic episodes caused a decrease in thyroid stimulating hormone, free T3 and free T4, which lasted over eighteen hours after the hypoglycemia. Dessein showed that HOMA score and Triglyceride/HDL ratios increased and that sub-clinical hypothyroidism was associated with insulin resistance. Dimitriadis, et al. showed that in hyperthyroid states, post-absorptive plasma glucose and insulin increased, plasma insulin responses increased, insulin receptor binding increased due to increased receptor affinity, insulin clearance increased and maximal insulin induced glucose uptake and oxidation increased. Risk of dysglycemia seems to be reduced with slightly hyper-thyroid function.

Arthritis and Inflammatory Risk—Dessein showed that in rheumatoid arthritis subjects, sub-clinical hypothyroid subjects had dysfunctions of glucose metabolism and insulin resistance. Innocencio showed that 52% of systemic sclerosis and 32% of rheumatoid arthritis subjects also had anti-thyroglobulin and/or anti-thyroperoxidase antibodies. This finding of silent autoimmune thyroiditis may contribute to the euthyroid sick syndrome seen in people with autoimmune diseases.

Neurological Risk—Klein showed that Hoffman's syndrome (increased muscle mass, stiffness and weakness) was associated with hypothyroidism. Cakir showed that there was an increased frequency of Dupuytren's contracture, carpal tunnel syndrome and decreased joint mobility in people who were sub-clinically hypothyroid. Madriaga showed a polymyositis-like syndrome in hypothyroid subjects. Tandeter showed an increased incidence of sub-clinical hypothyroidism in Parkinson's subjects. Brucker-Davis showed increased hearing loss in thyroid resistant subjects. Dolu showed abnormal EEG in sub-clinical hypothyroid subjects with lower skin conductance, lower fluctuation rates and prolonged onset latencies. Several investigators have shown an association between anxiety and depression and sub-clinical hypothyroidism. Valpato demonstrated that in 628 women older than 65 years there was a 1.97 relative risk of cognitive decline in sub-clinical hypothyroid women.

Bone Risk—Engler showed that in sub-clinical hyperthyroidism there were increases in bone resorption and bone formation parameters and an increased frequency of higher urinary pyridinoline and deoxypyrodinoline excretion. Meier, et al. demonstrated that in sub-clinical hypothyroid subjects who were given L-thyroxine to restore serum thyroid measurements to the euthyroid range, there was an increase in bone resorption. Kisakol showed that in sub-clinical hypothyroidism there was no disturbance in calcium metabolism, but in sub-clinical hyperthyroidism there was increased urinary calcium excretion, increased serum osteocalcin, and increased urinary deoxypyridinoline.

Pregnancy complication—Casey recently reported a three-fold increase in placenta previa and a two-fold increase in premature delivery in pregnant women with sub-clinical hypothyroidism.

There are various factors that can affect Thyroid Function. These factors include:

Peripheral Conversion of T4 to T3—Thyroid hormones are metabolized in peripheral tissues by deiodination, conjugation, deamination and decarboxylation enzyme reactions. Hepatic and renal pathology as well as stress states impact peripheral enzyme pathways. Toxic metals, chemical poisons, several drugs and nutrients may impact peripheral conversion. Vondra showed that there was a relationship between thyroid function and enzymes involved in glycolysis and cytoplasmic H2 transport from NADH2.

Mitochondrial Proton Leakage—Porter showed that mitochondrial proton leakage was related to uncoupling protein 3 (UCP3). de LP, et al. showed that UCP3 is regulated by T3 and causes mitochondrial uncoupling affecting resting metabolic rate. Reitman showed that free fatty acids appear to regulate UCP3 expression. Yu demonstrated that in euthyroid sick syndrome there is a decrease in activity of type 1 iodothyronine-5'-deiodinase (5'D-I) hepatic enzyme conversion of T4 to T3. This is believed to be a competitive inhibition by cytokines (IL-1 and IL-6). Hoch demonstrated that thyroid states regulate each cardiolipin property and are permissive, via the proton antenna, for proton leaks. Slow leakage in liposomes may be due to insufficient cardiolipin proton antennas.

Stressed States and Euthyroid Sick Syndrome—Schultes found that after a single episode of hypoglycemia, free T3 and free T4 were diminished and thyroid stimulating hormone increased up to 18 hours. Several investigators have found that in the Euthyroid Sick Syndrome and other stress states, thyroid function is severely decreased.

Cytokines—Yu demonstrated that Interleukins 1 and 6 competitively inhibit the T3 induction of 5'deiodinase RNA and enzyme activity in rat hepatocytes. Nagaya, et al. showed that activation of NF-kappa-B by TNF-alpha (which is elaborated in stress states) impairs T3 dependent induction of 5'deiodinase gene expression, which contributes to the Euthyroid Sick Syndrome. Rasmussen demonstrated that IL-1 alpha/beta in moderate and high concentrations reversibly inhibit thyroid cell function, while iL-1 beta in small doses stimulates thyroid cell function. This may contribute to the Euthyroid Sick Syndrome and/or autoimmune disease. The earliest stages involve antigen presenting cells interacting with the thyroid. In the later stages antigen specific and non-antigen specific immune cells are recruited to the thyroid and an inflammatory infiltrate is built. During this process cytokines, free nitric and oxygen radicals are released. Ren showed that Leukemia inhibitory factor (LIF), a neuroimmune pleiotropic cytokine, is produced in the thyroid gland. Thyroid stimulating hormone, IL-6, and glucocorticoid influence thyroid cell LIF expression. Kimur showed that IL-6 and IL-10 significantly correlated with thyroid stimulating hormone in acute MI subjects that developed Euthyroid Sick Syndrome. Bagriacik demonstrated that serum T3 and T4 levels are sharply and transiently reduced during the first 24 hrs following systemic antigen exposure. These findings suggest that during the early phase of antigen exposure the immune system directly participates in the regulatory control of thyroid hormone activity.

Nutrients—Barrows showed that very low carbohydrate diets caused decreases in resting metabolic rate, T3, and RT3 without affecting T4. Mathieson found that although dietary carbohydrate content had an influence on the magnitude of fall of serum T3, resting metabolic rate declined similarly in both high and low CHO diets. Poehlman showed that there was a slight, but insignificant, decline in T3 in vegetarians versus non-vegetarians. Dubois and Goldman could demonstrate no effect of hypothyroid on gastric secretion and emptying. Poehlman showed that acute exercise and caffeine ingestion had no effect on thyroid function. Berger, et al. showed that selenium supplementation had moderate effects on thyroid function with a quicker recovery in Euthyroid Sick subjects, although zinc and alpha tocopherol had no effect. Iron supplementation seems to increase resting metabolic rate and thyroxine levels, as does zinc in iron/zinc deficient individuals, but had no effect in iron/zinc sufficient. Clark showed that administration of kelp caused a significant and dose related increase in thyroid stimulating hormone and decrease in T3 and T4. Other sources of iodine performed similarly. In iodine deficient populations, supplementation of iodine improved thyroid function, but it reduces thyroid function in people who have adequate iodine. Benvenga showed that 1-carnitine decreases thyroid function by preventing its entry into the nucleus of cells, which improves bone resorption in hyperthyroid individuals.

Environmental Toxins—Rat studies by several investigators showed that PCB exposure resulted in severely decreased serum T4 and moderate decreases in serum T3. Tomasi showed that in rats exposed to fungicides there was a decrease in thyroid hormone and that there was a corresponding increase in T3 turn-over. Pelletier proposed that organochlorine pesticide residues residing in adipose tissue would be released and cause a decrease in thyroid function in obese individuals during weight loss programs. Garry studied pesticide applicators and found sub-clinical hypothyroidism in 5/144. Guven found that 31.8% of subjects who had been poisoned by organochlorines had Euthyroid Sick Syndrome.

Medications—Several authors have shown that seizure medications and lithium reduce thyroid function. Amiodorone has been implicated in thyroid dysfunction. Wang showed that a single dose of salsalate caused a decrease of T3 and T4 as well as an increase in reverse T3 which lasted up to 96 hrs. It was concluded that there was an acute release of T4 and T3 from circulatory transport proteins induced by an inhibitor of binding. This resulted in a large and rapid redistribution of T4 and T3 into tissue compartments associated with transiently reduced peripheral tissue 5'monodeiodination and deranged thyroid stimulating hormone regulation.

Physiological Measurements Related to Thyroid Function—Many investigators have used either estimations of resting energy expenditure, such as the Harris-Benedict equation, or direct measurements of resting metabolic rate to look at energy expenditure and energy requirements in a variety of populations. Many authors have demonstrated a decrease in resting metabolic rate with age and decreased thyroid function. Vondra showed the relationship between thyroid function and enzymes involved in glycolysis and hydrogen transport from NADH2, correlating achilles tendon reflexes and thyroid function. Khurana, Carel, Goodman and others have demonstrated statistically significant correlations between achilles tendon reflexes and thyroid function. Goulis demonstrated a similar effect using stapedial reflex. Findings have been consistent in a slowing of the firing interval of the reflex with decrease in thyroid function and a corresponding return to normal with treatment by thyroid medication. Body mass index and other physical markers seem to correlate. Being female and increasing age have shown correlations with thyroid dysfunction.

Serum Thyroid Tests—Scobbo showed great variability in serum thyroid stimulating hormone depending on the time of day samples were drawn and if the subject had fasted. Stockigt, et al. showed that there was no current methodology that accurately reflects the free T4 in undiluted serum.

Risk Associated with Hyperthyroidism—Gussakoo found no correlation between plasma thyrotropin and free thyroxine in elderly subjects with depression or cognitive dysfunction, but found that increased thyrotropin was correlated with increased longevity. Kisakol and others found that sub-clinical hyperthyroidism was associated with increased bone resorption, increased quality of life, increased lean body mass, increased functionality and increased longevity.

The above paragraphs note risks associated with thyroid dysfunction. These include hypothyroid and hyperthyroid dysfunctions. The many risks emphasize the importance of a simple and accurate device, system and method for monitoring thyroid dysfunction.

Thyroid dysfunction is also associated with various disease states, including Graves disease and Hashimoto's disease. Graves disease is a type of autoimmune disease that causes over-activity of the thyroid gland, causing hyperthyroidism. This over-activity is also referred to as "toxic diffuse goiter." The thyroid gland helps set the rate of metabolism which is the rate that the body uses energy. When the thyroid is too active, it makes more thyroid hormones than the body needs. High level of thyroid hormones can cause side effects such as weight lose, rapid heart rate and nervousness.

One aspect of Graves disease is the potential for developing thyroid storm. Patients presenting in thyroid storm report a dramatic weight loss and may complain of chest pain, palpitations, shortness of breath, tremor, nervousness, increased sweating, disorientation, and fatigue and in some cases, thyroid storm can cause death. Thyroid storm is also difficult to quickly diagnose. The device, system and method described herein allows a quick and relatively simple evaluation upon which a diagnosis of Graves disease may be made and the disease managed. Similarly, the device, system and method allow for a relatively quick diagnosis of thyroid storm.

Chronic thyroiditis (Hashimoto's disease) is an inflammation of the thyroid gland that frequently results in hyperthyroidism. The disease can cause cessation of thyroid function and is often treated with administering exogenous (either natural or synthetic) thyroid hormone. Thus, the device, system and method disclosed herein may be used to detect Hashimoto's disease. It has also been found that a subject taking either synthetic or natural thyroid hormone to manage Hashimoto's disease may experience a negative reaction in the sense that the subject's body ultimately recognizes the exogenous thyroid hormone and attacks the hormone. It has been found that by managing Hashimoto's disease, such as through use of the device, system and method described herein, the attack of the synthetic or natural exogenous hormone can be recognized. It has also been discovered that a shift from the one of the synthetic or natural thyroid hormone to the other manages the attack. Thus, upon the occurrence in the body of an attack on, for example, an exogenous synthetic thyroid hormone, the subject may shift from the synthetic thyroid hormone to a natural thyroid hormone and forestall the attack. Upon recognition by the body of the exogenous thyroid hormone, the subject may switch back to the synthetic hormone or another synthetic hormone. Such switching from natural to synthetic may be continued as necessary throughout the length of the disease.

Of the various reflex points in the body, a relatively easy place to test is the arm and the Brachioradialis was selected as an easy reflex muscle to identify.

In one trial, subjects were evaluated using a standardized Thyroid Symptom Questionnaire. Height and weight were measured on a standard clinic scale. Resting metabolic rate was predicted using the Harris-Benedict (HB) Equation. Resting metabolic rate was measured using a MedGem oxygen consumption device, which compared favorably to other valid measurements by way of example, the Douglas Bag, in clinical trials.

The trial was set up by measuring subjects for the following: Thyroid symptoms, age, gender, height, weight, body mass index, calculated resting metabolic rate (HB Equation), measured resting metabolic rate (Douglas Bag), measured Brachioradialis reflex intervals, and serum measurements of thyroid stimulating hormone (TSH), T3 uptake (T3U), T4, T7, cholesterol, LDL, HDL, and triglycerides. Some subjects also had free T3, free T4, Microsomal (TPO) autoantibody, thyroglobulin autoantibody, ACTH, and prolactin measurements.

Subjects that were taking thyroid medication received a dosage increase of the same medication. Subjects that had symptoms of thyroid dysfunction but were not currently taking thyroid medication were given a choice of thyroid treatments. All subjects were evaluated at 30 day intervals and dosages were increased until the Brachioradialis Reflexometry parameter of: Firing Interval-Pre-Firing Interval less than 66 to 120, in one embodiment less than 66 to 100 milliseconds (msec) was achieved. The less than 66 to 100 msec was established as follows.

Subjects became functionally normal and thyroid symptoms resolved when their medication doses were titrated using resting metabolic rate and Brachioradialis Reflexometry as the primary endpoints. Only 14 of over 800 subject interactions (1.7%) noted symptoms of nervousness, tachycardia, palpitations or insomnia, although thyroid stimulating hormone levels became less than 0.01 mU/L. ACTH, and prolactin levels remained normal in subjects with low thyroid stimulating hormone, indicating no suppression of pituitary function.

Brachioradialis Reflex measurements included: Pre-Firing Interval defined as the number of milliseconds from hammer strike to initiation of the Brachioradialis reflex response; Firing Interval defined as the number of milliseconds from initiation of the Brachioradialis reflex firing until return to baseline; and Firing-Pre-Firing which is the difference in milliseconds between those intervals.

Fasting serum specimens were collected for thyroid stimulating hormone, T3U, T4, T7 Cholesterol, LDL, HDL, and Triglycerides. Some subjects received free T3, free T4, RT3, TRH, Thyroid Microsomal (TPO) auto-antibody, Thyroglobulin auto-antibody, ACTH and Prolactin measurements. All serum measurements were collected in a clinic and processed by an independent laboratory. All serum measurements reflect their technique and norms.

Focusing on which factors are the best predictors of the dependent variable Resting Metabolic Rate (RMR), a stepwise Multiple Linear Regression Analysis (MLRA) was the analytical method used on a population of 563 subject encounters (N=563). After analysis of the independent variables with MLRA, it was determined that Subject Height (CM), Subject Weight (KG), Body Mass Index (BMI) of weight in kilograms divided by height in meters, squared, Pre-Firing Interval, Firing Interval and Firing Interval minus Pre-Firing Interval (Fire minus Prefire) were the best predictors of the dependent variable (resting metabolic rate).

An acceptable Multiple R value indicates approximated 65 percent of all variation is accounted for with the predictive equation being the Kail-Waters equation:

$$\text{RESTING METABOLIC RATE} = 2307.62 + [-7.53 (CM)] + [27.09 (KG)] + [-42.59 (BMI)] + [-45.47 (PREFIRE)] + [45.85 (FIRE)] + [-46.27 (FIRE-PREFI)]$$

In the preceding Kail-Waters equation, CM is height in centimeters, KG is weight in kilograms, BMI represents a body mass index which is a weight of a subject (in kilograms) divided by a height of the subject (in meters), squared, PRE-FIRE is a Pre-Firing Interval in milliseconds, FIRE is a Firing Interval in milliseconds, and FIRE-PREFI is a Firing Interval minus a Pre-Firing Interval.

Verification of the predictability of the equation was checked by computing a CRMR (Computed RMR) with the Kail-Waters equation for all subject encounters, and statistically comparing CRMR with measured resting metabolic rate using a Student t-test with a pooled variance. Ho: u1=u2 and Ha: u1≠u2

Based on the t-value of 0.0019, the Ho is accepted with u1=u2 or the mean of CRMR is statistically the same as the mean of resting metabolic rate with a non-significant 2-tailed probability of p=0.9985, giving relatively high credibility to the predictive equation.

Analysis of Thyroid Stimulating Hormone (TSH) with resting metabolic rate, Pre-Firing Interval, Firing Interval, Firing Interval—Pre-Firing Interval: A common medical practice is to use quantitative serum thyroid stimulating hormone levels as a basis for the treatment of thyroid pathologies. This supposition may not be correct. Using a Factor Analysis (Principal Components Analysis), it appears that thyroid stimulating hormone may not be as closely associated with resting metabolic rate as might be expected. The data suggests that thyroid stimulating hormone has relatively independent variation compared to the other selected variables in this study. Hashimoto's Disease and Thyroid Treatment: Six subjects in the study were discovered to have Hashimoto's disease. This was suspected if symptoms, resting metabolic rate and Brachioradialis measurements regressed in spite of increasing thyroid medication dosage. In every case, when microsomal (TPO) and/or thyroglobulin antibodies were found, the medication was switched from natural tissue to synthetic or visa versa. In every case, at the next measurement interval, symptoms, resting metabolic rate and Brachioradialis increased (showing more activity), although the antibodies remained high. This was seen as an indication that the antibodies did not recognize and bind with the new medication, thereby increasing receptor response.

Clinical investigators have long recognized that there was a discrepancy in reconciling a subject's symptoms and serum measurements of thyroid function. The hypothesis that physiological measurements of thyroid function were better indicators of functional status than serum measurements, and that many sub-clinically hypothyroid subjects were not receiving adequate treatment, which may increase their health risk, was confirmed by collected data. The unaccounted variance comes from stress events that occurred between measurement intervals that affected thyroid function.

Sub-clinical Hypothyroidism appears to greatly affect the subject's health risk of many chronic degenerative diseases. It is essential to treat this syndrome. Sub-clinical hypothyroidism seems to greatly increase the chronic degenerative diseases that are most prevalent. This population is not well identified by serum methods of thyroid function. In this population, the evidence supports the hypothesis that physiologic measurements of thyroid function are more accurate at identifying the sub-clinical hypothyroid state than serum measurements. Subjects became functionally normal and thyroid symptoms improved when their medication doses were titrated using resting metabolic rate and BR as the primary endpoints. Only 14 of over 800 subject interactions (1.7%) noted symptoms of nervousness, tachycardia, palpitations or insomnia although thyroid stimulating hormone levels became less than 0.01 mU/L in many subjects.

All measurements were made at baseline and 30 day intervals. Subjects already on thyroid medication continued it. Subjects on no medication were given the choice between Homeopathic Thyroid Formula, Thyroid nutritional co-factors without tissue, Thyroid Tissue OTC, Prescription natural thyroid or Prescription Synthetic Thyroid.

Doses of thyroid medication were increased until the Brachioradialis reflex parameter of: Firing Interval minus Pre-Firing Interval less than 66 to 100 msecs was achieved. If auto-immune disease (Hashimoto's) was identified, those subjects had their medication switched (tissue to synthetic or visa versa).

It appears that being slightly hyperthyroid has advantages in terms of increased longevity and decreased risk of several chronic degenerative diseases. Calcium supplementation of 1000 to 1500 mg/day as well as ipriflavone 900 mg/day to reduce bone resorption is important in subjects whose thyroid stimulating hormone is less than 0.3 mU/L.

Figure 4:
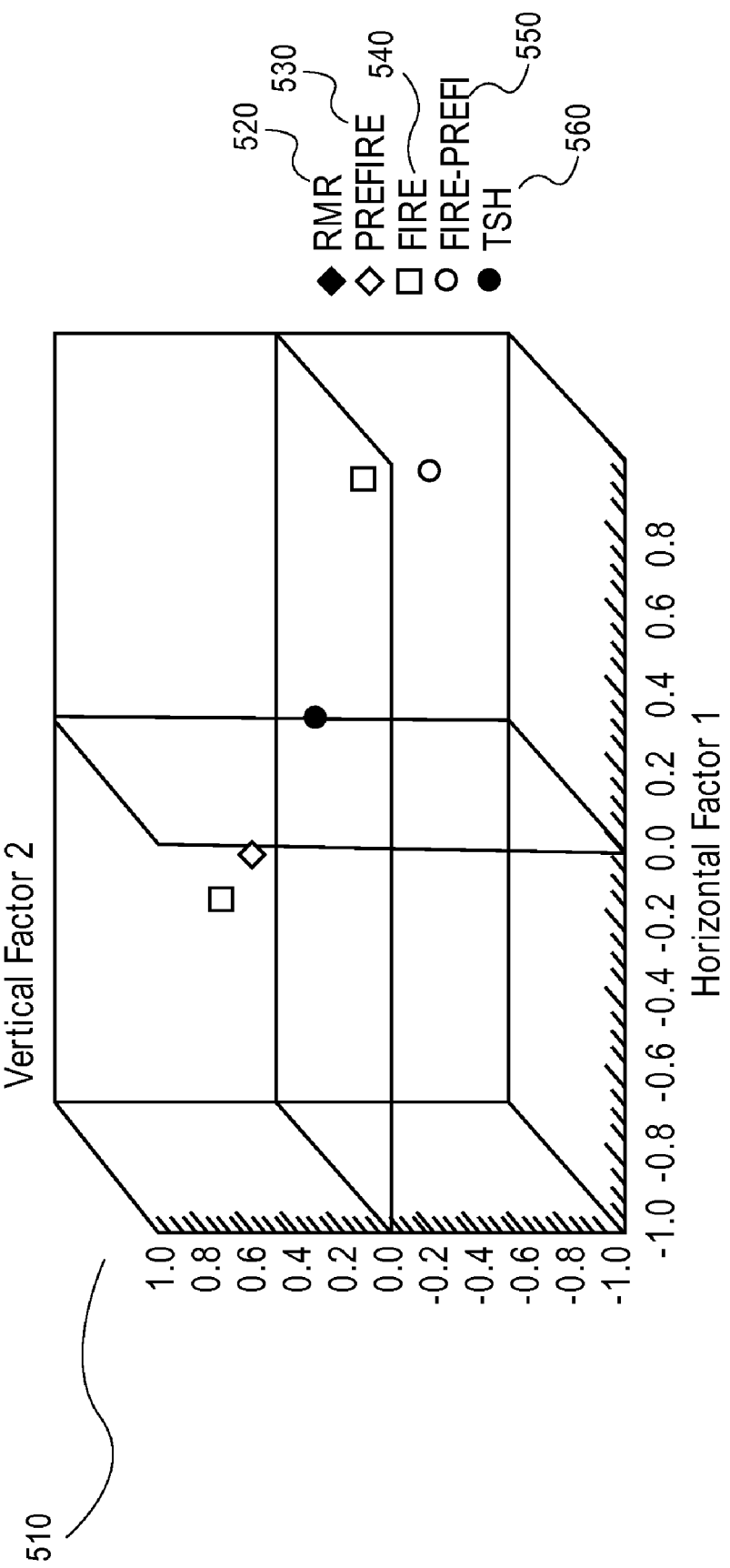
FIG. 4 shows a three-dimensional graphical representation of a resting metabolic rate and reflex parameters according to a principal components analysis.

Now referring to FIG. 4, this shows the Factor loadings 510—unrotated solution (Principal Components Analysis) Model, the Resting metabolic rate 520, Pre-Firing Interval 530, Firing Interval 540, Firing Interval minus Pre-Firing Interval 550 and thyroid stimulating hormone 560. The statistics analysis model illustrates that the resting metabolic rate and reflex parameters are related to each other, but thyroid-stimulating hormones are not related to any other of the noted parameters.

Figure 5:
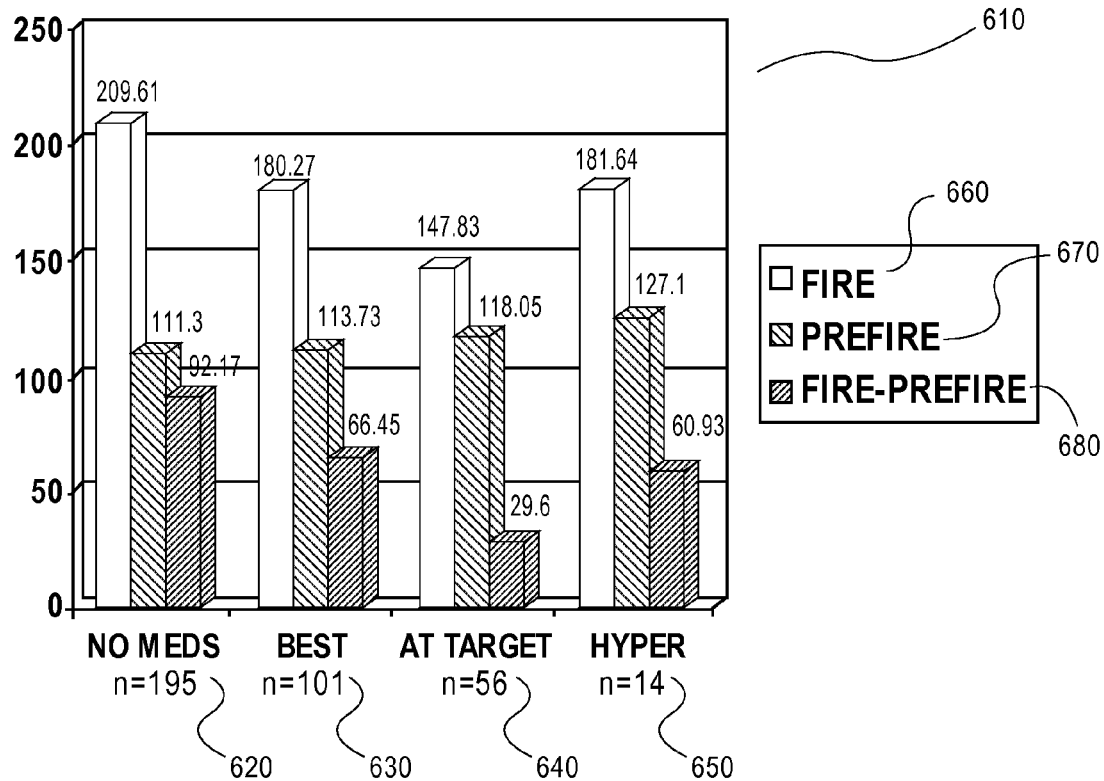
FIG. 5 shows a bar graph representation of reflex parameters including Firing Intervals, Pre-Firing Intervals and Firing Intervals minus Pre-Firing Intervals for a study group.
Figure 6:
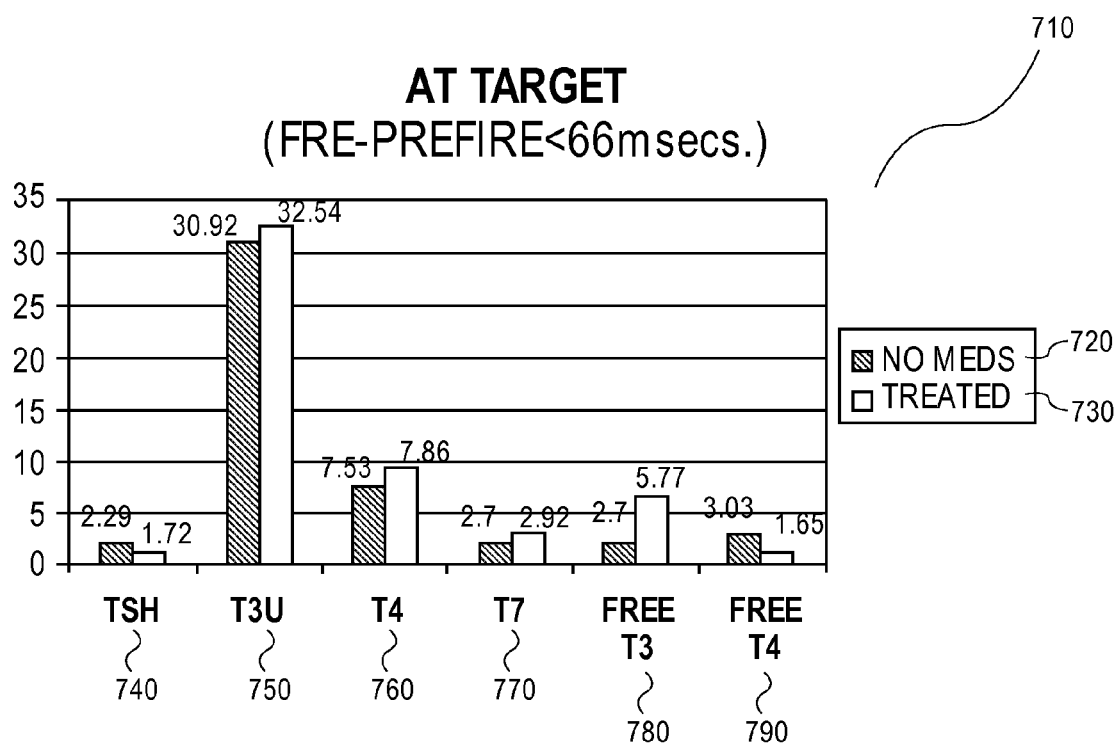
FIG. 6 shows a bar graph of Firing Interval minus Pre-Firing Interval for subjects in a study group both non-medicated and medicated at a target of less than 66 milliseconds.
Figure 7:
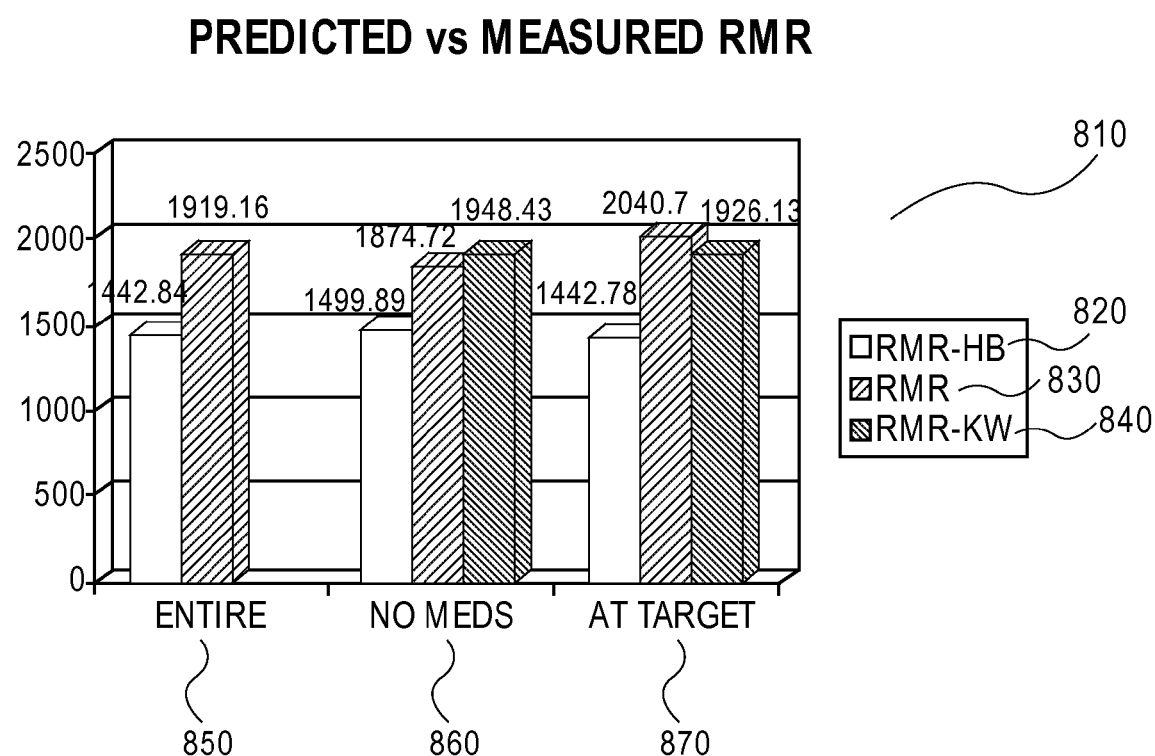
FIG. 7 shows a bar graph of the predicted resting metabolic rate for subjects in a study group determined by the Harris-Benedict equation, oxygen consumption device, and a Kail-Waters equation.

Now referring to the graphs in FIGS. 5, 6, and 7. FIG. 5 shows a reflex parameters graph 610, no medications 620, best 630, at target 640, hyperthyroid 650, Firing Interval 660, Pre-Firing Interval 670 and Firing Interval minus Pre-Firing Interval 680, wherein:

No medications 620 means no thyroid medication;

Best 630 means the best that those subjects had achieved although some had not reached targets;

At target 640 means that they met the target of greater than or equal to 355 kcal increase in resting metabolic rate; and Hyper 650 means that those subject experienced symptoms of hyperthyroid whether or not they had achieved targets.

The reflex parameters graph shows how the reflex intervals changed as the dose was increased.

FIG. 6 shows an at target graph 710 of Firing Interval minus Pre-Firing Interval less than 66 msecs, 720 no meds, 730 treated wherein:

TSH 740, means thyroid stimulating hormone;

T3U 750, is the uptake of the active form of the thyroid hormone;

T4 760, is the storage form of the thyroid hormone;

T7 770, is the free thyroxine index;

Free T3 780, is a more sensitive measurement of the active converted form of the thyroid hormone; and Free T4 790, is a more sensitive measurement of the storage uptake form of the thyroid hormone.

The at target graph of Firing Interval minus Pre-Firing Interval, less than 66 msecs, shows what happened to the serum thyroid hormone levels, in the at target group.

FIG. 7 shows the predicted vs measured resting metabolic rate (RMR) graph 810, with RMR-HB 820, RMR 830 and RMR-KW 840, wherein:

Entire 850 means the entire database, unstratified;

No medications 860 means the subpopulation of subjects on no thyroid medication;

At target 870 means the subpopulation of subjects that achieved the target;

RMR-HB 820 is resting metabolic rate calculated by the Harris-Benedict equation;

RMR 830 is the resting metabolic rate measured by the oxygen consumption device; and RMR-KW 840 is resting metabolic rate calculated by the Kail-Waters equation that was developed in this research.

The predicted vs measured resting metabolic rate (RMR) graph shows that the Kail-Waters pre-determined resting metabolic rate is a better predictor of resting metabolic rate than the currently accepted Harris-Benedict Equation.

The Predictability of the Brachioradialis Reflexometry method as developed is summarized as follows:

'Sensitivity' is the proportion of those that are hypothyroid that are correctly diagnosed. It is expressed as:

$$\frac{\text{True Positives}}{\text{True Positives} + \text{False Negatives}} = \frac{117}{117+1} = 0.992$$

'Specificity' is the proportion of those that are euthyroid that were correctly identified. It is expressed as:

$$\frac{\text{True Negatives}}{\text{True Negatives} + \text{False Positives}} = \frac{58}{58+6} = 0.906$$

'Predictive Value of a Positive Test' is the proportion of those with a positive test that are hypothyroid. It is expressed as:

$$\frac{\text{True Positives}}{\text{True Positives} + \text{False Positives}} = \frac{117}{117+6} = 0.951$$

'Predictive Value of a Negative Test' can be considered as the proportion of those with a negative test that are hypothyroid; which is expressed as:

$$\frac{\text{False Negatives}}{\text{False Negatives} + \text{True Negatives}} = \frac{1}{1+58} = 0.017$$

More commonly, 'Predictive Value of a Negative Test' is considered the proportion of those with a negative test who are euthyroid, which is expressed as:

$$\frac{\text{True Negatives}}{\text{False Negatives} + \text{True Negatives}} = \frac{58}{1+58} = 0.983$$

These calculations were based on the following:

Two targets of "normality" were developed: resting metabolic rate change more than 350 kcals and Firing Interval—Pre-Firing Interval less than 66 msecs. People that achieved the resting metabolic rate (gold standard) target had a mean resting metabolic rate measured at 2040.7 kcals. Therefore, the resting metabolic rate norm for euthyroid individuals was considered to be >2000 kcals being dependant on sex age, and size of the individual.

There were 179 people in the subpopulation of patients on no medication. There were 117 people identified as positive (hypothyroid) by resting metabolic rate criteria and 123 people identified as positive by Reflex criteria. There were 58 people identified as negative (euthyroid) by resting metabolic rate criteria and 57 people identified as negative by Reflex criteria. These numbers allow the construction of the following table:

|  | Gold Standard (RMR) (+) | Gold Standard (RMR) (−) |
|---|---|---|
| Positive Test (BR) | True Positives (117) | False Positives (6) |
| Negative Test (BR) | False Negatives (1) | True Negatives (58) |

Sub-clinical Hypothyroidism appears to greatly affect the subject's health risk of many chronic degenerative diseases. It is essential to treat this syndrome. Sub-clinical hypothyroidism seems to greatly increase the critical degenerative diseases that are most prevalent. This population is not well identified by serum methods of thyroid function. This may be the most under-identified chronic disease that affects a greater portion of the population than suspected.

In one embodiment, the device, system and method as described, is able to identify thyroid problems, including Hypothyroid, Hyperthyroid, Hashimoto's, Graves, among other conditions. The device is non invasive, accurate and from the results of the device an individual can be identified with the disease and dosed, after dosing, titrated, until the individual has equilibrated to a euthyroid state. The device can also identify if an individual can have their medications adjusted and can manage Hashimoto's and Graves disease.

In the preceding detailed description, reference is made to specific embodiments thereof. It will, however, be evident that various modifications and changes may be made thereto without departing from the broader spirit and scope of the following claims. The specification and drawings are, accordingly, to be regarded in an illustrative rather than a restrictive sense.

What is claimed is:

1. A method comprising:
   determining a pre-firing interval representing a first time period measured by sensors in which a reflex point is struck until an initiation of the reflex response;
   storing the pre-firing interval in a memory of a computer;
   determining a firing interval representing a second time period measured by sensors in which the reflex response is initiated and concluded;
   determining a time function by subtracting the pre-firing interval from the firing interval using a computer program; and
   correlating the time function to a hormone function.

2. The method of claim 1, wherein correlating the time functions to a hormone function comprises a thyroid hormone function.

3. The method of claim 1, further comprising determining a weight, a height, and a body mass index of the subject.

4. The method of claim 1, further comprising:
managing Hashimoto's disease based on the time function.

5. The method of claim 1, further comprising:
managing Graves disease based on the time function.

6. An apparatus comprising:
a striking instrument capable of delivering a kinetic energy to a reflex point of a subject;
a measurement instrument capable of being coupled to a subject and measuring a reflex response;
a processor comprising a memory and a machine-readable storage medium having a machine-readable program embodied therein comprising:
(1) instructions for determining a pre-firing interval representing a first time period in which a reflex point of a subject is struck and an initiation of the stimulation of the reflex point is sent to the brain of a subject to initiate a reflex response;
(2) instructions for determining a firing interval representing a second time period in which the reflex point of a subject having been struck and an initiation of a reflex response to the conclusion of the subject's reflex response; and
(3) instructions for subtracting the pre-firing interval from the firing interval.

7. The apparatus of claim 6, wherein the machine-readable program further comprises instructions for calculating a resting metabolic rate.

8. The apparatus of claim 7, wherein the instructions for calculating the resting metabolic rate is based on the equation:

Resting Metabolic Rate=2307.62+[−7.53 (height in centimeters)]−[27.09 (weight in kilograms)]+[−42.59 (body mass index)]+[−45.47 (pre-fire)]+[45.85 (Fire)]+[−42.67 (Fire−Pre-Fire)].

9. A non-transitory computer readable storage medium containing executable program instructions which when executed cause a digital processing system to perform a method comprising:
determining time periods in which a reflex point is struck and a reflex response is observed wherein the time periods include a pre-firing interval representing a time period in which a reflex point is struck until an initiation of the reflex response and a firing interval representing a time period in which the reflex response is initiated and concluded; and
determining a time function by subtracting the pre-firing interval from the firing interval; and
correlating the time function to a hormone function.

10. The machine-readable storage medium of claim 9, wherein the hormone function comprises thyroid hormone function.

11. The machine-readable storage medium of claim 9, wherein the method further comprises determining a weight, a height, and a body mass index of the subject.

12. The machine-readable storage medium of claim 9, wherein the method further comprises:
managing Hashimoto's disease based on the time periods.

13. The machine-readable storage medium of claim 9, wherein the method further comprises:
managing Graves disease based on the time periods.

* * * * *